US005599353A

United States Patent [19]

Cotteret et al.

[11] Patent Number: 5,599,353

[45] Date of Patent: Feb. 4, 1997

[54] COMPOSITION FOR THE OXIDATION DYEING OF KERATINOUS FIBERS COMPRISING 2-(β-HYDROXYETHYL)-PARA-PHENYLENE-DIAMINE, 2-METHYLRESORCINOL AND 3-AMINOPHENOL, AND DYEING PROCESS USING SUCH A COMPOSITION

[75] Inventors: Jean Cotteret, Verneuil Sur Seine; Marie-Pascale Audousset, Asnieres, both of France

[73] Assignee: L'Oreal, France

[21] Appl. No.: 460,879

[22] Filed: Jun. 5, 1995

[30] Foreign Application Priority Data

Jun. 6, 1994 [FR] France .................................. 94 06900

[51] Int. Cl.$^{6}$ .................................................. A61K 7/13

[52] U.S. Cl. .......................... 8/412; 8/406; 8/408; 8/410; 8/416; 8/421; 8/424

[58] Field of Search ............................... 8/406, 408, 410, 8/412, 416, 421, 424

[56] References Cited

U.S. PATENT DOCUMENTS

| | | | |
|---|---|---|---|
| 4,566,875 | 1/1986 | Grollien et al. | 8/408 |
| 4,840,639 | 6/1989 | Husemeyer et al. | 8/410 |
| 5,021,066 | 6/1991 | Aeby et al. | 8/408 |
| 5,224,965 | 7/1993 | Clausen et al. | 8/406 |
| 5,393,305 | 2/1995 | Cohen et al. | 8/408 |

FOREIGN PATENT DOCUMENTS

| | | |
|---|---|---|
| 0400330 | 12/1990 | European Pat. Off. . |
| 3706565 | 9/1988 | Germany . |
| 3834142 | 4/1990 | Germany . |
| 2168727 | 6/1986 | United Kingdom . |
| 2239265 | 6/1991 | United Kingdom . |
| WO80/00214 | 2/1980 | WIPO . |
| WO88/00823 | 2/1988 | WIPO . |

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

The invention relates to an oxidation dyeing composition for keratinous fibers containing, in a medium appropriate for dyeing, at least one oxidation dye precursor selected from 2-(β-hydroxyethyl)-para-phenylenediamine and its acid addition salts and at least one coupler selected from a combination of 2-methylresorcinol or at least one acid addition salt thereof with 3-aminophenol or at least one acid addition salt thereof. It also relates to the use of this composition for dyeing keratinous fibers and especially hair.

13 Claims, No Drawings

COMPOSITION FOR THE OXIDATION DYEING OF KERATINOUS FIBERS COMPRISING 2-(β-HYDROXYETHYL)-PARA-PHENYLENE-DIAMINE, 2-METHYLRESORCINOL AND 3-AMINOPHENOL, AND DYEING PROCESS USING SUCH A COMPOSITION

The present invention relates to a composition for the oxidation dyeing of keratinous fibers and in particular of human keratinous fibers comprising, in combination, 2-(β-hydroxyethyl) -para-phenylenediamine, 2-methylresorcinol and 3-aminophenol. It also relates to the use of such a composition.

It is known to dye keratinous fibers, and in particular human hair, with dyeing compositions containing oxidation dye precursors, in particular ortho- or para-phenylenediamines or ortho- or para-aminophenols, generally known as "oxidation bases", in combination with couplers, also known as coloring modifiers, more particularly meta-phenylenediamines, metaaminophenols and meta-diphenols, which make it possible to modify and enrich with highlights the "foundation" colorings obtained with the condensation products of oxidation bases.

The search, in the field of oxidation hair dyeing, is for oxidation dye precursors and couplers capable of producing, when they are combined, shades having a satisfactory resistance to light, to washes, to bad weather, to perspiration and to the various hair treatments to which hair may be subjected.

Until now, these shades have been obtained with dyes based on para-phenylenediamine. However, the use of paraphenylenediamine currently is being questioned for toxicological reasons.

In replacing para-phenylenediamine, it has already been proposed, in Patent Application WO 80/00214, to use paraphenylenediamine derivatives monohydroxyalkylated in the 2-position on the benzene ring.

In Patent EP-0,400,330 B1, a description has very particularly been given of a combination of 2-(β-hydroxyethyl) -para-phenylenediamine with a coupler chosen from resorcinol, 2-methylresorcinol, 4-chlororesorcinol, 3,4-methylenedioxyphenol, 3-aminophenol and N-(2-hydroxyethyl)-3, 4-methylenedioxyaniline. Example 2 in this document illustrates, in particular, the combination of 2-(β-hydroxyethyl)-para-phenylenediamine with resorcinol and 3-aminophenol.

However, this combination in Example 2 produces a shade which has little resistance to perspiration, which is expressed by a significant change in shade after the hair has been subjected to the action of perspiration.

Now, after much research directed at this question, the inventors have discovered that it is possible to obtain new non-toxic dyes which produce shades which are particularly highly resistant to perspiration, by combining 2-(β-hydroxyethyl) -para-phenylenediamine with 2-methylresorcinol and 3-aminophenol.

This discovery is the basis of the present invention.

The subject of the present invention is thus an oxidation dyeing composition for keratinous fibers, in particular for human keratinous fibers, such as hair, comprising, in a medium appropriate for dyeing, at least one oxidation dye precursor selected from 2-(β-hydroxyethyl)-para-phenylenediamine and its acid addition salts and at least one coupler selected from a combination of 2-methylresorcinol or at least one acid addition salt thereof with 3-aminophenol or at least one acid addition salt thereof.

The new dyes thus obtained make it possible to produce shades which are much more resistant to perspiration than those of the prior art, containing at least 2-(β-hydroxyethyl) -para-phenylenediamine in combination with resorcinol and 3-aminophenol.

Moreover, these new dyes, when they are applied, in particular, to hair which has been sensitized by a permanent deformation, have also proved to be much more resistant to shampoos than the dyes of the prior art combining 2-(β-hydroxyethyl) -para-phenylenediamine with 2-methylresorcinol or 2-(β-hydroxyethyl)-para-phenylenediamine with 3-aminophenol.

Another subject of the invention relates to the ready-to-use composition containing the various agents used for dyeing keratinous fibers defined above and an oxidizing agent.

The invention is also targeted at a process for dyeing keratinous fibers, and in particular human keratinous fibers such as hair, which comprises applying to these fibers at least one composition (A) containing, in a medium appropriate for dyeing, at least one oxidation dye precursor and at least two couplers as they have been defined above, the color being developed at alkaline, neutral or acidic pH using an oxidizing agent which is added to the composition (A) only at the time of use or which is present in a composition (B) separately applied simultaneously or sequentially.

Another subject of the invention is multi-compartment dyeing devices or "kits", the first compartment of which contains at least 2-(β-hydroxyethyl)-para-phenylenediamine, as oxidation dye precursor, and at least the combination of 2-methylresorcinol and 3-aminophenol, as couplers, and the second compartment of which contains an oxidizing agent.

Other characteristics, aspects, subjects and advantages of the invention will become still more clearly apparent on reading the description and examples which follow.

The acid salts which can be used according to the invention are preferably chosen from hydrochlorides, sulphates, hydrobromides and tartrates.

The concentration of oxidation dye precursor, or of its salts, can preferably vary from 0.01 to 10% by weight, approximately, with respect to the total weight of the dyeing composition and more preferentially still from 0.05 to 5% by weight, approximately.

The concentration of 2-methylresorcinol or of its salts can preferably vary from 0.005 to 5% by weight, approximately, with respect to the total weight of the dyeing composition and more preferentially still from 0.05 to 3% by weight, approximately.

The concentration of 3-aminophenol or of its salts can preferably vary from 0.005 to 5% by weight, approximately, with respect to the total weight of the dyeing composition and more preferentially still from 0.05 to 3% by weight, approximately.

The oxidizing agent is preferably chosen from hydrogen peroxide, urea hydrogen peroxide, alkali metal bromates and persalts such as perborates and persulphates. The use of hydrogen peroxide is particularly preferred.

The composition (A), which contains the combination of the dyes such as described above, can generally have a pH from 3 to 11 which can be adjusted to the chosen value either by means of basifying agents commonly used in dyeing keratinous fibers, such as aqueous ammonia, alkali metal carbonates, alkanolamines, for example mono-, di- and triethanoiamines and their derivatives, sodium hydroxide or potassium hydroxide or the compounds of formula:

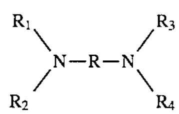

in which R is a propylene residue optionally substituted by a hydroxyl group or a $C_1$–$C_4$ alkyl radical and $R_1$, $R_2$, $R_3$ and $R_4$, simultaneously or independently of one another, represent a hydrogen atom or a $C_1$–$C_4$ alkyl or $C_1$–$C_4$ hydroxyalkyl radical, or by means of conventional acidifying agents, such as inorganic or organic acids such as, for example, hydrochloric, tartaric, citric and phosphoric acids.

The pH of the composition (B) containing the oxidizing agent such as defined above is such that, after mixing with the composition (A), the pH of the composition applied to human keratinous fibers preferably varies from 3 to 11. It is adjusted to the desired value using acidifying agents or optionally basifying agents which are well known in the state of the art, such as those described above.

The oxidizing composition (B) preferably consists of a hydrogen peroxide solution.

According to a preferred embodiment of the dyeing process of the invention, the dyeing composition (A) described above is mixed, at the time of use, with an oxidizing solution in an amount sufficient to develop a coloring. The mixture obtained is then applied to human keratinous fibers and left exposed for 5 to 40 minutes, preferably 15 to 30 minutes, after which the fibers are rinsed, washed with a shampoo, rinsed again and dried.

The dyeing compositions can also contain, in addition to the dyes defined above, other couplers and/or direct dyes, especially for modifying the shades or for enriching them with highlights.

The dyeing compositions can also contain anti-oxidizing agents. The latter can be chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid and are then generally present in an amount of from approximately 0.05 to 1.5% by weight with respect to the total weight of the composition.

The dyeing compositions also contain, in their preferred embodiment, surface-active agents which are well known in the art in a general amount of from approximately 0.5 to 55% by weight, and preferably from 2 to 50% by weight, with respect to the total weight of the composition; organic solvents, in an amount of from approximately 1 to 40% by weight, and in particular from 5 to 30% by weight, with respect to the total weight of the composition, or any other adjuvant which is cosmetically acceptable and known in the prior art in oxidation hair dyeing.

The composition applied to the hair can be provided in various forms, such as in liquid, cream or gel form or in any other form appropriate for carrying out dyeing of keratinous fibers, and especially of human hair. In particular, it can be packaged under pressure in an aerosol canister in the presence of a propellant and can form a foam.

Concrete examples illustrating the invention will now be given. The first step will be to define the tests used to evaluate the performances of the oxidation dyes according to the invention as regards their resistance to perspiration and to shampoo.

Resistance to perspiration:

A synthetic sweat solution with the following composition was used:

| | |
|---|---|
| NaCl | 1 g |
| Potassium hydrogenphosphate | 0.1 g |
| Histidine | 0.025 g |
| Lactic acid q.s. | pH 3.2 |
| Distilled water | q.s. for 100 g |

The locks of dyed hair were immersed in a crystallizing dish covered with a watch glass and containing this sweat solution and were left to stand for from 20 to 50 hours at 37° C. The locks were then rinsed and dried.

Resistance to shampoos (Ahiba-Texomat machine):

Locks of dyed hair were placed in a basket which was immersed in a solution of a standard shampoo. The basket was subjected to a vertical to-and-fro movement of variable frequency and to a rotational movement which reproduced the action of manual rubbing, which led to the formation of foam.

After testing for 3 minutes, the locks were removed and were rinsed and then dried.

EXAMPLE 1

The following dyeing composition, in accordance with the invention, was prepared:

| | |
|---|---|
| 2-(β-Hydroxyethyl)-para-phenylenediamine sulphate | 3.0 g |
| 2-Methylresorcinol | 0.60 g |
| 3-Aminophenol | 0.6 g |
| Cetyl alcohol | 15.0 g |
| Sodium sulphite | 0.3 g |
| Sodium lauryl ether sulphate as an aqueous solution containing 28% active material (A.M.) | 0.98 g A.M. |
| Aqueous ammonia solution containing 20% of $NH_3$ | 0.75 g A.M. |
| Demineralized water | q.s. for 100.0 g |

At the time of use, this composition was mixed, weight for weight, with hydrogen peroxide assaying at 20 volumes (6% by weight), with a pH of 3.

A mixture was obtained with a pH of 9.8.

This mixture was then applied to natural grey hair containing 90% of white hairs, for 30 minutes and at 40° C. After rinsing, washing with a shampoo, rinsing and drying, the hair was dyed and this dyed hair was then subjected to the test for resistance to perspiration (48 hours) described above.

In parallel, and according to the same process as that described above, hair was dyed using a dyeing composition of the prior art (Example 2 of Patent EP 0,400,330 B1), that is to say a counterpart of the composition according to the invention described above in which 2-methylresorcinol was replaced by an identical amount, by weight, of resorcinol. The hair dyed using the counterpart dyeing composition was subjected to the test for resistance to perspiration (48 hours) under the same conditions as the hair dyed using the composition according to the invention.

The shades were measured with a Minolta CM 2002 and expressed as Munsell values (ASTM D Standard 1535-68).

The shades of the dyed hair, expressed as Hue (H), before and then after it was subjected to the test for resistance to perspiration, are combined in the table below, with an indication of the difference in shade as AH:

| Value of the Hue | Before the perspiration test | After the perspiration test | ΔH |
|---|---|---|---|
| Composition according to the invention | 5.6 YR | 4.3 YR | 1.3 |
| Counterpart containing resorcinol | 4.1 R | 3.9 YR | 9.8 |

The hair dyed with the composition according to the invention was thus clearly observed, unexpectedly and surprisingly, to exhibit a markedly smaller change in the shade ($\Delta H=1.3$) in comparison with the hair dyed with the counterpart composition ($\Delta H=9.8$).

EXAMPLE 2

The following dyeing composition, in accordance with the invention, was prepared:

| | |
|---|---|
| 2-(β-Hydroxyethyl)-para-phenylene-diamine dihydrochloride | 0.60 g |
| 2-Methylresorcinol | 0.20 g |
| 3-Aminophenol | 0.20 g |
| Oleyl alcohol polyglycerolated with 4 mol of glycerol, containing 78% of active materials (A.M.) | 5.7 g A.M. |
| Oleyl alcohol polyglycerolated with 2 mol of glycerol | 4.0 g |
| Oleic acid | 3.0 g |
| Oleylamine containing 2 mol of ethylene oxide, sold under the name Ethomeen 012 by the Company Akzo | 7.0 g |
| Diethylaminopropyl laurylamino-succinamate, sodium salt, containing 55% of A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Monomethyl ether of propylene glycol | 9.0 g |
| Sodium metabisulphite as an aqueous solution containing 35% of A.M. | 0.46 g A.M. |
| Ammonium acetate | 0.8 g |
| Anti-oxidizing agent, sequestering agent | q.s. |
| Fragrance, preserving agent | q.s. |
| Aqueous ammonia solution containing 20% of $NH_3$ | 2.0 g A.M. |
| Demineralized water | q.s. for 100.0 g |

At the time of use, this composition was mixed, weight for weight, with hydrogen peroxide assaying at 20 volumes (6% by weight), with a pH of 3.

A mixture was obtained with a pH of 9.8.

This mixture was applied to permed grey hair containing 90% of white hairs, for 30 minutes. After rinsing, washing with a shampoo, rinsing and drying, the hair was dyed; then it was subjected to the test for resistance to shampoo described above.

Two comparative compositions were prepared in parallel which contain, as replacement for the combination according to the invention comprising 2-(β-hydroxyethyl) -para-phenylenediamine dihydrochloride +2-methylresorcinol +3-aminophenol, the following combinations:

Comparative composition (A):

2-(β-Hydroxyethyl)-para-phenylenediamine dihydrochloride (0.6 g)+2-methylresorcinol (0.4 g), Comparative composition (B):

2-(β-Hydroxyethyl)-para-phenylenediamine dihydrochloride (0.6 g)+3-aminophenol (0.4 g).

Evaluation of the resistance to shampoo:

The deterioration in the color between the dyed hair and that dyed which was subjected to a shampoo test as described above is expressed by means of the Nickerson equation which defines the color variation indices:

$$\Delta E=0.4C_0\Delta H+6\Delta V+3\Delta C;$$

this equation is described in the publication "Journal of the Optical Society of America", 1944, Sep., Vol. 34, No. 9, p. 550–570, the parameters H, V and C representing the parameters of the Munsell notation (ASTM Standard D 1535–68), which defines the color (H denoting the shade or Hue, V denoting the intensity or Value, C denoting the purity or Chromaticity and $C_0$ denoting the purity of the lock with respect to which it is desired to evaluate the difference in color).

The deteriorations in the color recorded with the composition according to the invention and those of the comparative compositions (A) and (B) were combined in the following table:

| Dyeing composition | Variation in color between dyed hair and dyed hair which has been subjected to a shampoo test (ΔE) |
|---|---|
| Composition of the invention | 1.66 |
| Comparative composition (A) | 4.15 |
| Comparative composition (B) | 8.58 |

As the deterioration in color became greater as the figure indicated (ΔE) became higher, the dyeing composition according to the invention was thus clearly observed, unexpectedly and surprisingly, to have a much better resistance to shampoo.

What is claimed is:

1. An oxidation dyeing composition (A) comprising, in a medium appropriate for dyeing, at least one oxidation dye precursor selected, from 2-(β-hydroxyethyl)-paraphenylenediamine and it acid addition salts and at least two couplers selected from a combination of 2-methylresorcinol or at least one acid addition salt thereof with 3-aminophenol or at least one acid addition salt thereof, said at least one oxidation dye precursor and at least two couplers selected from said combination being present in amounts effective to achieve oxidation dyeing in the presence of an oxidizing agent.

2. The dyeing composition according to claim 1, wherein said acid addition salts are selected from hydrochlorides, sulphates, hydrobromides and tartrates.

3. The dyeing composition according to claim 1, wherein said at least one oxidation dye precursor is present in a concentration of from 0.01 to 10% by weight with respect to the total weight of the composition; said 2-methylresorcinol or said at least one acid addition salt thereof is present in a concentration of from 0.01 to 5% by weight with respect to the total weight of the composition; and said 3-aminophenol or said at least one acid addition salt thereof is present in a concentration of from 0.01 to 5% by weight with respect to the total weight of the composition.

4. The dyeing composition according to claim 3, wherein said at least one oxidation dye precursor is present in a concentration of from 0.05 to 5% by weight; said 2-methylresorcinol or said at least one acid addition salt thereof is present in a concentration of from 0.05 to 3% by weight; and said 3-aminophenol or said at least one acid addition salt thereof is present in a concentration of from 0.05 to 3% by weight with respect to the total weight of the composition.

5. The dyeing composition according to claim 1, which is ready-to-use for dyeing keratinous fibers, wherein said composition further contains an oxidizing agent and has a pH from 3 to 11.

6. A process for dyeing keratinous fibers comprising the steps of:

applying to said fibers said oxidation dyeing composition (A) according to claim 1 and developing the color in alkaline, neutral or acidic medium using an oxidation agent which is added to said oxidation dyeing composition (A) only at the time of use or which is present in a composition (B) separately applied simultaneously or sequentially.

7. The process of claim 6, wherein said keratinous fibers are human keratinous fibers.

8. The process of claim 7, wherein said human keratinous fibers are hair.

9. A multi-compartment device or for dyeing keratinous fibers, wherein said device contains at least two compartments, one of which contains said oxidation dyeing composition (A) according to claim 1 and another of which contains a composition (B) comprising an oxidizing agent in a medium appropriate for dyeing.

10. The device of claim 9, wherein said keratinous fibers are human keratinous fibers.

11. The device of claim 10, wherein said human keratinous fibers are hair.

12. A method for dyeing human keratinous fibers comprising the step of applying said oxidation dye composition (A) according to claim 1 and a composition (B) to said human keratinous fibers, said oxidation dyeing composition (A) and composition (B) being obtained from a multi-compartment dyeing device or for dyeing keratinous fibers, wherein said device contains at least two compartments, one of which contains said oxidation dyeing composition (A) according to claim 1 and another of which contains a composition (B) comprising an oxidizing agent in a medium appropriate for dyeing.

13. The method of claim 12, wherein said human keratinous fibers are hair.

* * * * *

UNITED STATES PATENT AND TRADEMARK OFFICE

CERTIFICATE OF CORRECTION

PATENT NO.: 5,599,353

DATED: February 4, 1997

INVENTOR(S): Jean COTTERET et al.

It is certified that an error appears in the above-identified patent and that said Letters Patent is hereby corrected as shown below:

Claim 1, col. 6, line 45, "it" should read --its--;

Claim 9, col. 8, line 1, insert --kit-- after "or"; and

Claim 12, col. 8, line 16, insert --kit-- after "or".

Signed and Sealed this

First Day of July, 1997

Attest:

BRUCE LEHMAN

*Attesting Officer*

*Commissioner of Patents and Trademarks*